United States Patent
Khoo

(10) Patent No.: US 11,981,797 B2
(45) Date of Patent: May 14, 2024

(54) ELASTOMERIC COMPOSITION

(71) Applicant: INOOVA MATERIAL SCIENCE SDN BHD, Selangor (MY)

(72) Inventor: Siong Hui Khoo, Selangor (MY)

(73) Assignee: INOOVA MATERIAL SCIENCE SDN BHD, Selangor (MY)

( * ) Notice: Subject to any disclaimer, the term of this patent is extended or adjusted under 35 U.S.C. 154(b) by 902 days.

(21) Appl. No.: 16/968,454

(22) PCT Filed: Feb. 8, 2019

(86) PCT No.: PCT/MY2019/050011
§ 371 (c)(1),
(2) Date: Aug. 7, 2020

(87) PCT Pub. No.: WO2019/156550
PCT Pub. Date: Aug. 15, 2019

(65) Prior Publication Data
US 2020/0399450 A1 Dec. 24, 2020

(30) Foreign Application Priority Data

Feb. 9, 2018 (MY) ............................. 2018700532

(51) Int. Cl.
| | |
|---|---|
| A61B 42/10 | (2016.01) |
| C08K 3/36 | (2006.01) |
| C08K 5/00 | (2006.01) |
| C08K 5/053 | (2006.01) |
| C08K 5/09 | (2006.01) |
| C08K 5/17 | (2006.01) |
| C08K 5/5435 | (2006.01) |
| C08L 9/04 | (2006.01) |
| C08L 9/08 | (2006.01) |
| C08L 11/02 | (2006.01) |
| C08L 27/18 | (2006.01) |

(52) U.S. Cl.
CPC .............. *C08L 11/02* (2013.01); *A61B 42/10* (2016.02); *C08K 3/36* (2013.01); *C08K 5/0025* (2013.01); *C08K 5/005* (2013.01); *C08K 5/053* (2013.01); *C08K 5/09* (2013.01); *C08K 5/17* (2013.01); *C08K 5/5435* (2013.01); *C08L 9/04* (2013.01); *C08L 9/08* (2013.01); *C08L 27/18* (2013.01); *C08L 2207/04* (2013.01); *C08L 2312/08* (2013.01)

(58) Field of Classification Search
None
See application file for complete search history.

(56) References Cited

U.S. PATENT DOCUMENTS

| | | | |
|---|---|---|---|
| 2003/0125463 A1 | 7/2003 | Tatsu et al. | |
| 2004/0115444 A1 | 6/2004 | Janssen et al. | |
| 2005/0271842 A1 | 12/2005 | Triebes et al. | |
| 2014/0165263 A1 | 6/2014 | Pham et al. | |
| 2014/0323256 A1* | 10/2014 | Yoshida | F16G 5/14 474/271 |
| 2017/0342241 A1* | 11/2017 | Fukumine | C08K 5/17 |
| 2018/0016419 A1* | 1/2018 | Shimizu | C08L 23/14 |

FOREIGN PATENT DOCUMENTS

AU 2013362879 B2 6/2014

* cited by examiner

*Primary Examiner* — Megan McCulley
(74) *Attorney, Agent, or Firm* — Muncy, Geissler, Olds & Lowe, P.C.

(57) ABSTRACT

The present application relates to a crosslinked composition. The composition comprises an elastomer, a silane compound, a liquid fluorocarbon and a crosslinker, preferably an epoxy silane. The crosslinked composition may be used in the production of any elastomeric article manufactured through a dipping process, such as a glove.

9 Claims, No Drawings

ELASTOMERIC COMPOSITION

BACKGROUND OF THE INVENTION

Rubber, whether obtained naturally from latex or synthesized by polymerization, comprise polymers chains with varying lengths.

Acrylonitrile butadiene rubber comprises copolymers of nitrile and butadiene monomers, and are generally more resistant to chemicals, oil, and able to withstand heat of up to 110° C. A higher concentration of nitrile in acrylonitrile butadiene rubber results in an increased resistance to chemicals and oils, making acrylonitrile butadiene rubber an ideal rubber for the production of protective articles. However, nitrile also decreases the flexibility of acrylonitrile butadiene rubber, making it unideal for articles such as gloves, where flexibility is important for control of fingers.

Chloroprene rubber comprises copolymers of chlorine and butadiene monomers which typically display good resistance to ozone cracking, heat, and chemicals, as the chlorine in the polymer reduces the reactivity of the rubber to many oxidizing agents. However, chloroprene rubber tends to harden over time, and degrades in the presence of some common chemicals, such as hydrochloric acid, acetone, or xylene.

Natural rubber comprises mainly of polymers of isoprene. Used extensively with many applications, some physical properties of natural rubber comprise high resilience, elongation, and tensile strength. Despite this, the major drawback of the use of natural rubber is the ability of latex proteins in the rubber to induce an allergic reaction in users.

Synthetic polyisoprene rubber is the synthetic version of natural rubber with is known for having a strong resistance to inorganic chemicals and resilient tear strength. However, synthetic polyisoprene rubber tends to deteriorate when in contact with oxygen and light, and is unsuitable for use with hydrocarbons or organic liquids.

Polyurethane rubber comprises isocyanate and polyol. Whilst polyurethane typically has strong tear resistance and flexibility, it is unable to provide adequate protection as it is susceptible to heat and chemicals.

Styrene butadiene rubber is produced either through free-radical solution polymerization or by emulsion polymerization. The presence of styrene in the composition gives the rubber an improvement in strength and abrasion resistance, but has inferior fatigue resistance to natural rubber. Additionally, styrene butadiene rubber is vulnerable to heat and oxygen, and has poor chemical resistance.

Butadiene rubber is typically formed from the polymerization of 1,3-butadiene. Most commonly used for automobile tires, the rubber has a high resistance to tear. However, butadiene rubber has low friction, thus making it very slippery on wet surfaces.

The properties and limitations of the rubbers can be drastically altered and improved by a process of crosslinking the polymer chains.

For crosslinking of the polymer chains to be successful, the process should be carried out under strict monitoring to ensure that the scorch resistance, acceleration, and cure time of the rubber is efficient. When carried out properly, the physical properties of the rubber are enhanced, with improved malleability, strength, and elasticity.

Typically, rubbers are crosslinked at a high temperature using a conventional sulphur vulcanization system which require the addition of sulphur and accelerators. Unfortunately, these additives are potential contaminants that affect the end product. For example, the addition of sulphur may cause glove discolouration, especially if in contact with traces of metal. Accelerators, on the other hand, are potential irritants that are capable of inducing an allergic reaction in users.

Some examples include a glove formulation according to U.S. Pat. No. 6,874,165 B2 with thickening agent of carboxymethyl cellulose for making a NBR glove having an elongation at break about 550-680% as measured according to the American Society for Testing and Materials (ASTM). U.S. Pat. No. 6,000,061 A discusses a glove comprising a blend of chloroprene rubber and a carboxylated synthetic butadiene rubber with an elongation at break about 600% to 720%.

However, the disadvantage of both aforementioned documents is the presence of potential contaminants and/or irritants in the glove. Particularly, U.S. Pat. No. 6,874,165 discusses the use of an accelerating agent in the glove formulation, while U.S. Pat. No. 6,000,061 discusses the addition of sulphur in the glove. Accelerating agents, such as thiurams, mercaptobenzothiazole, carbamates or any of their derivatives may be potential irritants, with the ability to cause chronic dermatitis in users. Further, any traces of sulphur particles present on the glove may be a contaminant; for example, causing discolouration of the glove.

A need therefore exists for crosslinked rubber which addresses the above limitations which is hypoallergenic and less likely to induce an allergic reaction in its users.

SUMMARY OF THE INVENTION

The present invention aims to provide a crosslinked composition which overcomes, or at least reduces, the known limitations of the present rubbers.

Particularly, some improvements in rubber articles produced from said crosslinked composition include an improvement in flexibility, durability, and elasticity.

The present invention also aims to provide a hypoallergenic elastomeric composition which is less likely to induce an allergic reaction in all users, including those with Type I and IV hypersensitivities.

This and other objectives of the invention are achieved by a composition comprising an elastomer, a liquid fluorocarbon, a silane compound, and a crosslinker having a formula of:

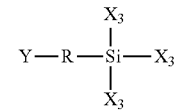

wherein Y is a functional group selected from primary and substituted amino, epoxy, methacryl, vinyl, mercapto, urea, or isocyanate;
R is a linking group between the functional group Y and a silicon atom, wherein R is propylene or ethyl;
Si is the silicon atom; and
$X_3$ are hydrolysable groups selected from methoxy, ethoxy, or isopropoxy.

Preferably, the crosslinker is an epoxy silane.

The composition can comprise an elastomer selected from any one of polyurethane rubber, polychloroprene rubber, synthetic polyisoprene rubber, acrylonitrile butadiene rubber, natural rubber, styrene butadiene rubber, or butadiene rubber.

The silane compound is a mixture of silicon dioxide and 2-amino-2 methylpropanol, while the liquid fluorocarbon can comprise tetrafluoroethylene or a mixture of liquid fluorocarbon emulsion.

The composition may further comprise an antioxidant, liquid surfactant, and carboxylic acid.

DETAILED DESCRIPTION OF THE INVENTION

Embodiments of the present invention will now be described in a more detailed manner, and the scope of the invention will be fully conveyed to those skilled in the art. However, it should be understood that the present disclosure is not intended to limit the invention to the precise forms as disclosed, but rather, provided so that the disclosure will be thorough and complete.

The present embodiment relates to a crosslinked elastomeric composition. The composition, comprising an elastomer, a liquid fluorocarbon, a silane compound, and a crosslinker, is capable of producing a composition with improved mechanical properties when manufactured into a product.

The crosslinker comprises a general formula of:

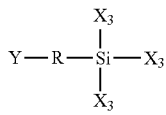

wherein Y is a functional group selected from primary and substituted amino, epoxy, methacryl, vinyl, mercapto, urea, or isocyanate;
R is a linking group between the functional group Y and a silicon atom, wherein R is propylene or ethyl;
Si is the silicon atom; and
$X_3$ are hydrolysable groups selected from methoxy, ethoxy, or isopropoxy.

In the present embodiment, the composition comprises 0.5 to 10% weight of the crosslinker. The crosslinker is preferably an epoxy silane.

In one embodiment, the epoxy silane is [3-(2,3-epoxypropoxy)propyl]trimethoxysilane, preferably added to the composition at 0.5 to 3% weight of the composition.

In another embodiment, the epoxy silane is a mixture comprising [3-(2,3-epoxypropoxy)propyl]trimethoxysilane and methanol, preferably added to the composition at 0.5 to 3% weight of the composition. The mixture comprises about 99.7 to 99% weight of [3-(2,3-epoxypropoxy)propyl] trimethoxysilane, and about 0.3 to 1% weight of methanol.

In yet another embodiment, the epoxy silane is a cycloaliphatic epoxy silane, comprising β(3,4-epoxycyclohexyl)-ethyltriethoxysilane and preferably added to the composition at 0.5 to 5% weight of the composition.

The crosslinker can also comprise any one of the following: octyltriethoxysilane, methyltriethoxysilane, methyltrimethoxysilane, tris-[3-(trimethoxysilyl)propyl] isocyanurate, hexadecyltrimethoxysilane, vinyltriethoxysilane, vinyltrimethoxysilane, vinyl-tris-(2-methoxyethoxy) silane, γ-methacryloxypropyltrimethoxysilane, methacrylamido-silane, γ-methacryloxypropyltriethoxysilane, γ-methacryloxypropyl-tris-(2-propoxy)silane, β-(3,4-Epoxycyclohexyl)ethyltrimethoxysilane, γ-glycidoxypropyltrimethoxysilane, γ-glycidoxypropyltriethoxysilane, or 3-glycidoxypropylmethyldiethoxysilane, although it should not be limited to as such.

In the present embodiment, the composition comprises 1 to 5% weight of the silane compound.

The silane compound is a mixture comprising silicon dioxide and 2-amino-2 methylpropanol, comprising about 10 to 30% weight of silicone dioxide, 1 to 3% weight of 2-amino-methylpropanol, 2 to 5% weight of liquid surfactant, and 62 to 87% weight of water. The liquid surfactant preferably comprises non-ionic or anionic surfactants.

In the present embodiment, the composition comprises 0.5 to 15% weight of liquid fluorocarbon.

In one embodiment, the liquid fluorocarbon comprises a mixture of liquid fluorocarbon and liquid emulsifier, dipropylene glycol, acetic acid, and water. The weight of the liquid fluorocarbon comprises 25 to 30% of liquid fluorocarbon and liquid emulsifier, for example, 95 to 99.5% weight of liquid fluorocarbon and 0.5 to 5% weight of liquid emulsifier, 8 to 12% of dipropylene glycol, 0.1 to 0.2% of acetic acid, and 57.8 to 66.9% of water.

The liquid emulsifier may be any one of a liquid anionic, non-ionic, or cationic surfactant known in the art.

The liquid fluorocarbon may be any one of a liquid anionic, non-ionic, or cationic fluorocarbon known in the art.

In an alternative embodiment, the liquid fluorocarbon is tetrafluoroethylene with the chemical formula of $C_2F_4$.

The composition according to the present embodiment, comprising 51 to 98% weight of elastomer.

The elastomer may comprise polyurethane (PU) rubber, polychloroprene (CR) rubber, synthetic polyisoprene (PI) rubber, acrylonitrile butadiene rubber (NBR), natural rubber (NR), styrene butadiene rubber (SBR), or butadiene rubber (BR).

In one embodiment, the elastomer is PU rubber, and comprises 5 to 30% weight of isocyanide and 70% to 95% of polyol. More preferably, the PU rubber comprises 20 to 25% weight of isocyanide and 75 to 80% weight of polyol.

In an alternative embodiment, the elastomer in the composition is CR rubber, and comprises 51 to 74% weight of 1,3-butadiene and 15 to 50% weight of chlorine. More preferably, the CR rubber comprises about 18% chlorine and 82% butadiene.

The composition may also comprise 0.1 to 3% weight of an activator and/or 2 to 8% weight of carboxylic acid. The activator is preferably a divalent oxide, or more particularly, zinc oxide, which assists in achieving a high efficiency during crosslinking.

In another embodiment, the elastomer is PI rubber and comprises preferably 90 to 98% weight of CIS 1,4 and 2 to 10% weight of trans 1,4.

In yet another embodiment, the elastomer is NBR rubber and comprises 51 to 74% weight of 1,3-butadiene and 23 to 42% weight of acrylonitrile. More preferably, the NBR rubber comprises 30% weight of acrylonitrile and 65% weight of 1,3-butadiene. The composition may also comprise 2 to 8% weight of carboxylic acid.

In another embodiment, the elastomer is NR rubber and preferably comprises 99% of CIS 1,4 and 1% trans 1,4.

In another embodiment, the elastomer is SBR rubber and comprises 5 to 30% weight of styrene and 62 to 93% weight of 1,3-butadiene. The elastomer may also comprise 2 to 8% weight of carboxylic acid. More preferably, the composition of the SBR rubber comprises 15 to 20% weight of styrene, 74 to 81% weight of 1,3-butadiene, and 4 to 6% weight of carboxylic acid.

In yet another embodiment, the elastomer is BR rubber and comprises 92 to 98% weight of 1,3-butadiene. The elastomer may also comprise 2 to 8% weight of carboxylic acid. More preferably, the BR rubber comprises a composition of 94 to 96% weight of 1,3-butadiene and 4 to 6% weight of carboxylic acid.

The carboxylic acid in any of the embodiments described above is preferably methacrylic acid.

Liquid surfactant may also be added to any of the elastomers to increase the stability of the composition. Liquid surfactant may be added in a range of 2 to 3% weight of the composition.

The liquid surfactant preferably comprises anionic or non-ionic liquid surfactants.

An antioxidant may also be added to any of the embodiments above to increase the stability of the composition by inhibiting oxidation in the composition. The antioxidant added can be selected from phenolic, phosphite, amine, or any antioxidants known for preventing the degradation of latex articles. In an alternative embodiment, the composition comprises 0.1 to 5% weight of antioxidant.

Various embodiments of the composition have been described in detail above. One example the composition is suitable for is the production of an elastomeric article manufactured through a latex dipping process. Such an example of said elastomeric article produced through a latex dipping process is a glove.

The composition according to any of the embodiments above are able to produce an elastomeric article where some improvements include an increase in flexibility, tear resistance, and an overall improvement in shelf life. These and other improvements will be described in more detail below.

Method

An example of a method for producing a glove from the present composition is disclosed. However, it should be noted again that the composition can also be used for any elastomeric article produced from the dipping method.

TABLE 1

Process flow for producing a glove according to the present composition for polyurethane (PU) rubber, polychloroprene (CR) rubber, synthetic polyisoprene (PI) rubber, acrylonitrile butadiene rubber (NBR), natural rubber (NR), styrene butadiene rubber (SBR), or butadiene rubber (BR).

| Process flow | PU/CR/PI/NBR/NR/SBR/BR glove glove process flow | | | | | |
| --- | --- | --- | --- | --- | --- | --- |
| | Temp- ° C. | Dwell time- sec | Concentration- % | pH- Value | Water flow rate- LPM | Viscosity Cps- spinder 1 60 rpm, 25° C. |
| 1) former cleaning | | | | | | |
| a) Option 2 | | | | | | |
| 1) Acid | 35~66 | 3~8 | 1.5~4 | 2~4 | 2~3 | |
| 2) Base | 35~50 | 8~20 | 4~8 | 10~14 | 2~3 | |
| 3) Rinse - Clean water | 55~70 | 10~15 | | 7~9.5 | 3~15 | |
| b) Option 2 | | | | | | |
| 1) Surfactant | 60~50 | 20~40 | 2~4 | 6~8 | 2~3 | |
| 2) Rinse - clean water | 55~70 | 10~15 | | 7~9.5 | 3~13 | |
| 2) Coagulant Dipping Tank | | | | | | |
| a) Option 2 | 40~60 | 12~21 | | 6~8.5 | | 4~5 |
| 1) Wetting agent | | | 0.05~3 | | | |
| 2) Calcium Nitrate/Calcium Chloride | | | 5~20 | | | |
| a) Option 2 | 40~50 | 12~21 | | 6~8.5 | | 4~9 |
| 1) Metallic Stearic- Zinc, Cal, K, Mg | | | 0.5~3 | | | |
| 2) Wetting agent | | | 0.05~3 | | | |
| 3) Calcium Nitrate/Calcium Chloride | | | 5~20 | | | |
| b) Option 3 | 40~60 | 12~21 | | 7~9.5 | | 4~9 |
| Calcium carbonate | | | 3~8 | | | |
| Wetting agent | | | 0.05~3 | | | |
| Calcium Nitrate/Calcium Chlorate | | | 3~20 | | | |
| 3) Coagulant Oven - Infra ray/Hot air/ far Infra ray/Internally heated former | 66~140 | 30~150 | | | | |
| 4) Latex dipping tank | | | | | | |
| a) Option 1- Single dipping | 25~38 | 14~30 | 14~40 | 6~8 | | 3~10 |
| b) Option 2- Double dipping | | | | | | |
| First Dipping | 25~38 | 14~30 | 14~40 | 6~8 | | 3~10 |
| Drying Oven - Infra Ray/Hot air/Far infra ray/internally heated former | 60~120 | 30~150 | | | | |
| Second Dipping | 25~38 | 14~30 | 14~40 | 6~8 | | 3~10 |
| 4) Gelling Oven-Infra Ray/Hot air/Far infra ray/internally heated former | 40~120 | 30~150 | | | | |
| 5) Pre Leaching - Clean Water | 40~80 | 60~160 | | | 20~100 | |
| 6) Doning Surface coating - PUD/PA/Flourine | 20~40 | 5~15 | 0.5~3 | 5~10 | | 3~10 |
| 7) Polymer Drying Oven - Infra Ray/Hot air/Far infra ray/internally Heated former | 30~120 | 30~150 | | | | |
| 8) Beading Station | | | | | | |
| 9) Drying&Curing Oven - Infra Ray/Hot air/ Far infra ray/internally heated former | 70~150 | 300~1200 | | | | |
| 10) Post leaching - Clean Water | 40~80 | 60~160 | | | 20~100 | |
| 11) Cooling - Clean Water | | | | | | |
| 12) Chlorination | | | | | | |
| 13) Neutralizer | | | | | | |
| 14) Rinse | | | | | | |
| 15) Donning Coating - Optional | | | | | | |
| Option 1- Calcium Carbonate/Constructs | 30~50 | 5~8 | 3~8 | 9~10 | | 3~10 |
| Option 2- Moisturizer | Plants/Fruit/Vege active&etc) | 25~35 | 5~8 | 1~5 | 5~8 | | 3~10 |

TABLE 1-continued

Process flow for producing a glove according to the present composition for polyurethane (PU) rubber, polychloroprene (CR) rubber, synthetic polyisoprene (PI) rubber, acrylonitrile butadiene rubber (NBR), natural rubber (NR), styrene butadiene rubber (SBR), or butadiene rubber (BR).

| | PU/CR/PI/NBR/NR/SBR/BR glove glove process flow | | | | | |
|---|---|---|---|---|---|---|
| Process flow | Temp- ° C. | Dwell time- sec | Concentration- % | pH-Value | Water flow rate- LPM | Viscosity Cps-spinder 1 60 rpm, 25° C. |
| Option 3- chlorofluorocarbons (CFCs) | 25~35 | 5~8 | 0.5~5 | 5~8 | | 3~10 |
| 16)Drying Oven - Infra Ray/Hot air/Far Infra ray/internally heated former | 70~150 | 80~240 | | | | |
| 17)Stripping station - Manual/Auto Striping | | | | | | |
| 18)Collecting glove - Manual/Auto Stripping | | | | | | |

TABLE 2

Process flow for producing for producing a glove according to the present composition synthetic polyisoprene (PI), acrylonitrile butadiene (NBR), natural rubber (NR), styrene butadiene rubber (SBR), or butadiene rubber (BR).

| | PI/NR/NBR/SBR/BR glove process flow | | | | | |
|---|---|---|---|---|---|---|
| Process flow | Temp- ° C. | Dwell time- sec | Concentration- % | pH-Value | Water flow rate- LPM | Viscosity Cps-spinder 1, 60 rpm, 25° C. |
| 1]former cleaning | | | | | | |
| a)Option 1 | | | | | | |
| 2)Acid | 35~60 | 3~8 | 1.5~4 | 2~4 | 2~3 | |
| 2)Base | 35~60 | 8~20 | 4~8 | 10~14 | 2~3 | |
| 3]Rinse - Clean water | 55~70 | 10~15 | | 7~9.5 | 3~15 | |
| b}Option 2 | | | | | | |
| 1)Surfactant | 60~80 | 20~40 | 2~4 | 6~8 | 2~3 | |
| 2)Rinse - Clean water | 55~70 | 10~15 | | 7~9.5 | 3~15 | |
| 2)Coagulant Dipping Tank | | | | | | |
| a)Option 1 | 40~60 | 12~21 | | 6~8.5 | | 4~9 |
| 1)Wetting agent | | | 0.05~5 | | | |
| 2)Calcium Nitrate/Calcium Chloride | | | 5~20 | | | |
| a)Option 2 | 40~60 | 12~21 | | 6~8.5 | | 4~9 |
| 2)Metallic Stearic- Zinc, Cal, K, Mg | | | 0.5~3 | | | |
| 2)Wetting agent | | | 0.05~3 | | | |
| 2)Calcium Nirate/Calcium· Chloride | | | 5~20 | | | |
| b)Option 3 | 40~60 | 12~21 | | 7~9.5 | | 4~9 |
| Calcium carbonate | | | 3~8 | | | |
| Wetting agent | | | 0.05~3 | | | |
| Calcium Nitrate/Calcium Chloride | | | 5~20 | | | |
| 3)Coagulant Oven - Infra ray/Hot air/Far infra ray/internally heated former | 60~140 | 30~150 | | | | |
| 4) Latex clipping tank | | | | | | |
| a)Option 1 - Single dipping | 25~38 | 14~30 | 14~40 | 6~8 | | |
| b)Option 2- Double dipping | | | | | | |
| First Dipping | 25~38 | 14~30 | 14~40 | 6~8 | | 3~10 |
| Drying Oven - Infra ray/Hot air/Far Infra ray/internally heated former | 60~120 | 30~150 | | | | |
| Second Dipping | 25~38 | 14~30 | 14~40 | 6~8 | | 3~10 |
| 4)Gelling Oven-Infra Ray/Hot air/Far infra ray/internally heated former | 40~120 | 30~150 | | | | |
| 5)Pre Leaching - Clean Water | 40~80 | 60~160 | | | 20~100 | |
| 6)Doning Surface coating - PUD/PA/Flouride | 20~40 | 5~15 | 0.5~3 | 5~10 | | 3~10 |
| 7)Polymer Drying Oven - Infra Ray/Hot air/Far infra ray/internally Heated former | 30~120 | 30~150 | | | | |
| 8)Beading Station | | | | | | |
| 9)Drying&Curing Oven- Infra Ray/Hot air/Far infra ray/Internally heated fanner | 70~150 | 300~1200 | | | | |
| 10)Post Leaching - Clean Water | 40~80 | 60~160 | | | 20~60 | |
| 11)Cooling - Clean Water | 30~50 | 10~20 | | | 10~20 | |
| 12)Chlorination | 25~30 | 20~40 | 0.05~0.12 | | | |
| 13)Neutralizer | 30~50 | 8~20 | | 5~8 | 5~10 | |
| 14)Rinse | 40~80 | 25~40 | | | 20~60 | |
| 15)Donning Coating - Optional | | | | | | |
| Option 1 - Calcium Carbonate/Constructs | 30~50 | 5~8 | 3~8 | 9~0 | | 3~10 |
| Option 2 - Moisturizer ǀ Plants/Fruit/Vege active&etc) | 25~35 | 5~8 | 1~5 | 5~8 | | 3~10 |

TABLE 2-continued

Process flow for producing for producing a glove according to the present composition synthetic polyisoprene (PI), acrylonitrile butadiene (NBR), natural rubber (NR), styrene butadiene rubber (SBR), or butadiene rubber (BR).

| | PI/NR/NBR/SBR/BR glove process flow | | | | | |
|---|---|---|---|---|---|---|
| Process flow | Temp-°C. | Dwell time-sec | Concentration-% | pH-Value | Water flow rate-LPM | Viscosity Cps-spinder 1, 60 rpm, 25° C. |
| Option 3 - chlorofluorocarbons (CFCs) | 25~35 | 5~8 | 0.5~5 | 5~8 | | 3~10 |
| 16)Drying Oven - Infra Ray/Hot air/Far infra ray/Internally heated former | 70~150 | 80~240 | | | | |
| 17)Stripping station - Manual/Auto Striping | | | | | | |
| 18)Collecting glove - Manual/Auto Stripping | | | | | | |

\* Coagulant/Latex is applicable for single dipping, double dipping, or more dipping profile
\* The processes above are applicable for additional post processes, such as chlorination, DI water wash, moisturization, polymer coating.
\* PU and CR rubbers are not applicable for the chlorine process Coagulant/Latex is applicable for single dipping, double dipping, or more dipping profile The processes above are applicable for additional post processes, such as chlorination, DI water wash, moisturization, polymer coating.

PU and CR rubbers are not applicable for the chlorine process

Results 9 different compositions were used to produce different versions of NBR gloves. Each version was then subjected to the same test to not only test its mechanical properties, but to also be compared against a control glove, i.e. one similar to gloves sold in the market, to see if the additives in the composition influenced the results in any way. The results are discussed below.

TABLE 3

Composition of produced NBR gloves

| Version | Elastomer | Composition |
|---|---|---|
| V1 (control) | NBR | Zinc oxide, sulphur, dithiocarbamates, phenolic antioxidant |
| V2 | NBR | β(3,4-epoxycyclohexyl)-ethyltriethoxysilane, tetrafluoroethylene, zinc oxide |
| V3 | NBR | β(3,4-epoxycyclohexyl)-ethyltriethoxysilane, tetrafluoroethylene |
| V4 | NBR | β(3,4-epoxycyclohexyl)-ethyltriethoxysilane, silicon dioxide and 2-amino-2 methylpropanol, zinc oxide |
| V5 | NBR | β(3,4-epoxycyclohexyl)-ethyltriethoxysilane, silicon dioxide and 2-amino-2 methylpropanol |
| V6 | NBR | [3-(2,3-epoxypropoxy)propyl]trimethoxysilane and methanol, tetrafluoroethylene, zinc oxide |
| V7 | NBR | [3-(2,3-epoxypropoxy)propyl]trimethoxysilane and methanol, tetrafluoroethylene |
| V8 | NBR | [3-(2,3-epoxypropoxy)propyl]trimethoxysilane and methanol, silicon dioxide and 2-amino-2 methylpropanol, Zinc oxide |
| V9 | NBR | [3-(2,3-epoxypropoxy)propyl]trimethoxysilane and methanol, silicon dioxide and 2-amino-2 methylpropanol |

TABLE 4

Tensile strength of the different versions of the gloves

| | Unaged | | | | | Aged | | | | |
|---|---|---|---|---|---|---|---|---|---|---|
| | Tensile Strength (MPa) | Elongation (%) | M100% (Mpa) | M300% (Mpa) | M500% (Mpa) | Tensile Strength (MPa) | Elongation (%) | M100% (Mpa) | M300% (Mpa) | M500% (Mpa) |
| V1 | 22-30 | 480-550 | 2-3 | 4-9 | 8-15 | 25-35 | 450-500 | 3-4 | 5-10 | 9-16 |
| V2 | 25-35 | 520-600 | 1.6-2.8 | 2.5-6.5 | 6-12 | 23-35 | 530-660 | 2.5-3.3 | 3.6-8.3 | 7-13 |
| V3 | 16-22 | 600-750 | 1-2 | 1.5-2.5 | 5-8 | 17-23 | 620-750 | 1.2-2.2 | 1.7-2.6 | 5.5-8 |
| V4 | 20-30 | 550-630 | 1.8-3.3 | 2.1-5.8 | 5.5-11 | 22-33 | 580-600 | 2.2-3.0 | 3.1-7.7 | 6.6-12.8 |
| V5 | 15-20 | 650-780 | 0.9-1.8 | 1.3-2.3 | 4.8-7.5 | 16-22 | 670-800 | 1.1-2.1 | 1.5-3.4 | 5.6-7.7 |
| V6 | 25-33 | 580-700 | 0.8-1.6 | 1.2-2.0 | 5.0-6.8 | 25-30 | 580-700 | 0.9-1.8 | 2.0-3.1 | 4.0-6.0 |
| V7 | 16-25 | 680-800 | 0.7-1.5 | 1.1-1.9 | 4.5-6.5 | 15-25 | 700-830 | 0.8-1.6 | 1.1-2.0 | 4.5-6.5 |
| V8 | 26-36 | 600-800 | 1.0-1.8 | 1.4-2.2 | 5.1-6.9 | 26-36 | 600-800 | 1.1-2.1 | 2.2-3.3 | 4.2-6.2 |
| V9 | 15-18 | 800-1050 | 0.6-1.4 | 1.0-1.8 | 4.0-6.0 | 15-18 | 800-1050 | 0.6-1.5 | 1.0-1.8 | 4.0-6.0 |

The tensile strength of the gloves was tested according to American Society for Testing and Materials (ASTM) tests D6319-10.

While half the gloves (V3, V5, V7, and V9) were found to have a lower tensile strength than the control (V1), the tensile strength results of the gloves with the additives still met ASTM requirements, and are thus able to offer sufficient protection to the user.

The control, V1, was found to have the highest modulus of elasticity whether at 100%, 300%, or 500% for aged and unaged gloves. Subsequently, this in turn affected the elongation at break %, where V1 was found to exhibit lower results than the gloves with additives, V2-V9.

The improvement in glove elongation and modulus of elasticity of gloves V2-V9 are highly indicative of the effectiveness of the additives added to the composition. Less force is required to stretch the gloves to 100%, 300%, and 500%, therefore proving the softness and flexibility of the glove. As a result, the gloves are able to have a higher elongation at break %.

Further, gloves V2-V9 show that no major differences between the recorded results of aged gloves (aged for 7 days at 70° C.) and unaged gloves, indicating a longer shelf-life for the gloves with additives.

The gloves with additives therefore exhibited an improvement in softness and flexibility when compared with the control, yet at the same time meeting the ASTM requirements for tensile strength.

TABLE 5

| | | | Swelling index (%) of the gloves | | | | | | | | | | | | | |
|---|---|---|---|---|---|---|---|---|---|---|---|---|---|---|---|---|
| | | Time | 0 min | 1 min | 2 min | 3 min | 4 min | 5 min | 6 min | 7 min | 8 min | 9 min | 10 min | 15 min | 20 min | 25 min | 30 min |
| Acetonitrile | V1 | 0 | 28 | 28 | 28 | 28 | 28 | 28 | 28 | 28 | 28 | 28 | 28 | 28 | 28 | 28 |
| | V2 | 0 | 24 | 24 | 24 | 28 | 28 | 28 | 28 | 28 | 28 | 28 | 28 | 28 | 28 | 28 |
| | V3 | 0 | 24 | 24 | 24 | 28 | 28 | 28 | 28 | 28 | 28 | 28 | 28 | 28 | 28 | 28 |
| | V4 | 0 | 28 | 28 | 28 | 28 | 28 | 28 | 28 | 28 | 28 | 28 | 28 | 28 | 28 | 32 |
| | V5 | 0 | 30 | 30 | 30 | 30 | 30 | 30 | 32 | 32 | 32 | 32 | 32 | 32 | 32 | 32 |
| | V6 | 0 | 20 | 28 | 28 | 28 | 28 | 28 | 28 | 28 | 28 | 28 | 28 | 28 | 28 | 28 |
| | V7 | 0 | 28 | 28 | 28 | 28 | 28 | 28 | 28 | 28 | 28 | 28 | 28 | 28 | 28 | 28 |
| | V8 | 0 | 20 | 20 | 20 | 20 | 20 | 20 | 20 | 20 | 20 | 20 | 20 | 20 | 20 | 20 |
| | V9 | 0 | 28 | 28 | 28 | 28 | 28 | 28 | 28 | 28 | 28 | 28 | 28 | 28 | 28 | 28 |
| Isopropyl Alcohol | V1 | 0 | 4 | 4 | 4 | 4 | 4 | 4 | 4 | 4 | 4 | 8 | 8 | 8 | 8 | 8 |
| | V2 | 0 | 4 | 4 | 4 | 4 | 4 | 4 | 4 | 4 | 8 | 8 | 8 | 8 | 8 | 8 |
| | V3 | 0 | 4 | 4 | 4 | 4 | 4 | 4 | 4 | 4 | 8 | 8 | 8 | 8 | 8 | 8 |
| | V4 | 0 | 0 | 0 | 4 | 4 | 4 | 4 | 4 | 4 | 4 | 8 | 8 | 8 | 8 | 8 |
| | V5 | 0 | 4 | 4 | 4 | 4 | 4 | 4 | 8 | 8 | 8 | 8 | 8 | 10 | 10 | 10 |
| | V6 | 0 | 4 | 4 | 4 | 4 | 4 | 4 | 4 | 4 | 4 | 4 | 4 | 4 | 4 | 4 |
| | V7 | 0 | 0 | 0 | 0 | 0 | 4 | 4 | 4 | 4 | 4 | 4 | 4 | 4 | 4 | 4 |
| | V8 | 0 | 0 | 0 | 0 | 0 | 0 | 0 | 0 | 0 | 0 | 0 | 4 | 4 | 4 | 4 |
| | V9 | 0 | 0 | 4 | 4 | 4 | 4 | 4 | 4 | 4 | 4 | 8 | 8 | 8 | 8 | 8 |
| Acetone | V1 | 0 | 68 | 76 | 76 | 76 | 76 | 76 | 76 | 76 | 76 | 76 | 76 | 76 | 76 | 76 |
| | V2 | 0 | 60 | 68 | 68 | 68 | 68 | 68 | 68 | 68 | 68 | 68 | 68 | 72 | 72 | 72 |
| | V3 | 0 | 60 | 60 | 60 | 60 | 60 | 60 | 60 | 60 | 60 | 60 | 60 | 60 | 60 | 60 |
| | V4 | 0 | 60 | 64 | 64 | 64 | 64 | 64 | 64 | 64 | 64 | 64 | 64 | 64 | 64 | 64 |
| | V5 | 0 | 64 | 64 | 64 | 64 | 68 | 68 | 68 | 68 | 68 | 68 | 70 | 70 | 70 | 70 |
| | V6 | 0 | 60 | 68 | 68 | 68 | 76 | 76 | 76 | 76 | 76 | 76 | 76 | 76 | 76 | 76 |
| | V7 | 0 | 60 | 68 | 76 | 76 | 76 | 76 | 76 | 78 | 78 | 80 | 80 | 80 | 80 | 80 |
| | V8 | 0 | 40 | 40 | 40 | 40 | 40 | 40 | 40 | 40 | 40 | 40 | 40 | 40 | 40 | 40 |
| | V9 | 0 | 68 | 68 | 68 | 68 | 68 | 68 | 68 | 68 | 68 | 72 | 72 | 72 | 72 | 72 |
| MEK | V1 | 0 | 100 | 100 | 100 | 100 | 100 | 100 | 100 | 100 | 100 | 100 | 100 | 100 | 100 | 100 |
| | V2 | 0 | 124 | 132 | 132 | 140 | 140 | 140 | 140 | 140 | 140 | 140 | 140 | 140 | 140 | 140 |
| | V3 | 0 | 100 | 100 | 100 | 100 | 100 | 100 | 100 | 100 | 100 | 100 | 100 | 100 | 100 | 100 |
| | V4 | 0 | 84 | 92 | 100 | 100 | 100 | 100 | 104 | 104 | 108 | 108 | 108 | 108 | 108 | 108 |
| | V5 | 0 | 96 | 96 | 96 | 96 | 96 | 96 | 96 | 96 | 96 | 96 | 96 | 96 | 96 | 96 |
| | V6 | 0 | 108 | 124 | 132 | 132 | 132 | 136 | 136 | 140 | 140 | 140 | 140 | 140 | 140 | 140 |
| | V7 | 0 | 124 | 132 | 132 | 132 | 132 | 132 | 132 | 132 | 132 | 132 | 132 | 132 | 132 | 132 |
| | V8 | 0 | 60 | 64 | 68 | 68 | 65 | 72 | 76 | 76 | 76 | 76 | 76 | 76 | 76 | 76 |
| | V9 | 0 | 92 | 92 | 92 | 92 | 92 | 92 | 92 | 92 | 92 | 92 | 92 | 92 | 92 | 92 |

| | | | Swelling Index (%) | | | | | | | | | | | | | |
|---|---|---|---|---|---|---|---|---|---|---|---|---|---|---|---|---|
| | | Time | 0 min | 1 min | 2 min | 3 min | 4 min | 5 min | 6 min | 7 min | 8 min | 9 min | 10 min | 15 min | 20 min | 25 min | 30 min |
| Toulene | V1 | 0 | 44 | 44 | 44 | 44 | 44 | 44 | 44 | 44 | 44 | 44 | 44 | 44 | 44 | 44 |
| | V2 | 0 | 40 | 44 | 44 | 44 | 44 | 44 | 44 | 44 | 44 | 44 | 44 | 44 | 44 | 44 |
| | V3 | 0 | 44 | 44 | 44 | 44 | 44 | 44 | 44 | 44 | 44 | 44 | 44 | 44 | 44 | 44 |
| | V4 | 0 | 28 | 44 | 44 | 44 | 44 | 44 | 44 | 44 | 44 | 44 | 44 | 44 | 44 | 44 |
| | V5 | 0 | 44 | 44 | 44 | 44 | 44 | 44 | 44 | 44 | 44 | 44 | 44 | 44 | 44 | 44 |
| | V6 | 0 | 44 | 48 | 52 | 52 | 52 | 52 | 52 | 52 | 52 | 52 | 52 | 52 | 52 | 52 |
| | V7 | 0 | 44 | 48 | 48 | 52 | 52 | 52 | 52 | 52 | 52 | 52 | 52 | 52 | 52 | 52 |
| | V8 | 0 | 28 | 28 | 28 | 28 | 28 | 28 | 28 | 28 | 28 | 28 | 28 | 28 | 28 | 28 |
| | V9 | 0 | 44 | 48 | 52 | 52 | 52 | 52 | 52 | 52 | 52 | 52 | 52 | 52 | 52 | 52 |
| Ethanol | V1 | 0 | 4 | 4 | 4 | 4 | 8 | 8 | 8 | 8 | 8 | 8 | 8 | 8 | 8 | 8 |
| | V2 | 0 | 4 | 4 | 4 | 8 | 8 | 8 | 8 | 8 | 8 | 8 | 8 | 8 | 8 | 8 |
| | V3 | 0 | 0 | 4 | 4 | 12 | 12 | 12 | 12 | 12 | 12 | 12 | 12 | 12 | 12 | 12 |
| | V4 | 0 | 0 | 8 | 8 | 12 | 12 | 12 | 12 | 12 | 12 | 12 | 12 | 12 | 12 | 12 |
| | V5 | 0 | 0 | 12 | 12 | 12 | 12 | 12 | 16 | 16 | 16 | 16 | 16 | 16 | 16 | 16 |

TABLE 5-continued

Swelling index (%) of the gloves

| | | | | | | | | | | | | | | | | |
|---|---|---|---|---|---|---|---|---|---|---|---|---|---|---|---|---|
| | V6 | 0 | 0 | 0 | 0 | 0 | 0 | 0 | 0 | 0 | 0 | 4 | 4 | 4 | 4 | 4 |
| | V7 | 0 | 0 | 0 | 0 | 0 | 0 | 0 | 0 | 0 | 0 | 0 | 0 | 0 | 0 | 0 |
| | V8 | 0 | 0 | 4 | 4 | 4 | 4 | 4 | 4 | 4 | 4 | 4 | 8 | 8 | 8 | 8 |
| | V9 | 0 | 0 | 4 | 4 | 4 | 4 | 4 | 4 | 4 | 4 | 4 | 4 | 4 | 4 | 4 |

| | Time (min) | 0 min | 1 min | 2 min | 3 min | 4 min | 5 min | 6 min | 7 min | 8 min | 9 min | 10 min | 15 min | 20 min | 25 min | 30 min |
|---|---|---|---|---|---|---|---|---|---|---|---|---|---|---|---|---|
| NaOH | V1 | 0 | 0 | 0 | 0 | 0 | 0 | 0 | 0 | 0 | 0 | 0 | 0 | 0 | 0 | 0 |
| | V2 | 0 | 0 | 0 | 0 | 0 | 0 | 0 | 0 | 0 | 0 | 0 | 0 | 0 | 0 | 0 |
| | V3 | 0 | 0 | 0 | 0 | 0 | 0 | 0 | 0 | 0 | 0 | 0 | 0 | 0 | 0 | 0 |
| | V4 | 0 | 0 | 0 | 0 | 0 | 0 | 0 | 0 | 0 | 0 | 0 | 0 | 0 | 0 | 0 |
| | V5 | 0 | 0 | 0 | 0 | 0 | 0 | 0 | 0 | 0 | 0 | 0 | 0 | 0 | 0 | 0 |
| | V6 | 0 | 0 | 0 | 0 | 0 | 0 | 0 | 0 | 0 | 0 | 0 | 0 | 0 | 0 | 0 |
| | V7 | 0 | 0 | 0 | 0 | 0 | 0 | 0 | 0 | 0 | 0 | 0 | 0 | 0 | 0 | 0 |
| | V8 | 0 | 0 | 0 | 0 | 0 | 0 | 0 | 0 | 0 | 0 | 0 | 0 | 0 | 0 | 0 |
| | V9 | 0 | 0 | 0 | 0 | 0 | 0 | 0 | 0 | 0 | 0 | 0 | 0 | 0 | 0 | 0 |
| DCM | V1 | 0 | 104 | 108 | 112 | 116 | 116 | 116 | 116 | 116 | 116 | 116 | 116 | 120 | 120 | 120 |
| | V2 | 0 | 100 | 104 | 108 | 108 | 108 | 112 | 112 | 116 | 116 | 116 | 120 | 120 | 124 | 124 |
| | V3 | 0 | 104 | 104 | 104 | 104 | 104 | 104 | 104 | 104 | 104 | 104 | 104 | 104 | 104 | 104 |
| | V4 | 0 | 108 | 108 | 112 | 112 | 116 | 116 | 116 | 116 | 116 | 116 | 116 | 116 | 116 | 116 |
| | V5 | 0 | 120 | 120 | 120 | 120 | 128 | 128 | 128 | 128 | 128 | 128 | 128 | 128 | 128 | 128 |
| | V6 | 0 | 144 | 148 | 156 | 160 | 164 | 164 | 164 | 164 | 164 | 164 | 164 | 164 | 164 | 164 |
| | V7 | 0 | 140 | 144 | 148 | 156 | 156 | 156 | 156 | 156 | 156 | 156 | 156 | 156 | 156 | 156 |
| | V8 | 0 | 84 | 100 | 100 | 100 | 100 | 100 | 100 | 100 | 100 | 104 | 108 | 108 | 108 | 108 |
| | V9 | 0 | 116 | 116 | 120 | 120 | 120 | 120 | 120 | 120 | 120 | 120 | 120 | 120 | 120 | 120 |

The chemical resistance of the gloves was tested by immersing the gloves in chemicals such as acetonitrile, isopropyl alcohol, acetone, methyl ethyl ketone (MEK), toluene, ethanol, sodium hydroxide (NaOH), and dichloromethane (DCM) for 30 minutes at room temperature, where the lower the value of the swelling index (%), the more resistant the glove is to the chemicals. The swelling index (%) is measured according to:

$$Q = \frac{W_2 - W_1}{W_1}$$

wherein Q is the swelling index (%), $W_1$ is the initial weight and $W_2$ is the swollen weight after being immersed in the chemicals for 30 minutes at room temperature.

Of all the gloves, at least half of the V2-V9 gloves showed similar, if not improved, chemical resistance for each tested chemical when compared against the control glove. This further indicates that the additives play a role in maintaining, if not improving, chemical resistance of the glove.

TABLE 6

Stress retention (%) and stress relaxation (%) of the gloves

| Formulation | Time | 0 min | 1 min | 2 min | 3 min | 4 min | 5 min |
|---|---|---|---|---|---|---|---|
| V1 | Stress Retention (%) | 100.00 | 67.27 | 61.91 | 58.34 | 56.56 | 54.77 |
| | Stress Relaxation (%) | 0.00 | 32.73 | 38.09 | 41.66 | 43.44 | 45.23 |
| V2 | Stress Retention (%) | 100.00 | 54.17 | 48.81 | 45.24 | 43.45 | 41.67 |
| | Stress Relaxation (%) | 0.00 | 45.83 | 51.19 | 54.76 | 56.55 | 58.33 |
| V3 | Stress Retention (%) | 100.00 | 49.84 | 45.10 | 32.85 | 31.44 | 30.03 |
| | Stress Relaxation (%) | 0.00 | 50.16 | 54.90 | 67.15 | 68.56 | 69.97 |
| V4 | Stress Retention (%) | 100.00 | 49.17 | 43.16 | 40.01 | 37.84 | 36.35 |
| | Stress Relaxation (%) | 0.00 | 50.83 | 56.84 | 59.99 | 62.16 | 63.65 |
| V5 | Stress Retention (%) | 100.00 | 44.53 | 38.97 | 36.04 | 33.87 | 32.44 |
| | Stress Relaxation (%) | 0.00 | 55.47 | 61.03 | 63.96 | 66.13 | 67.56 |
| V6 | Stress Retention (%) | 100.00 | 44.11 | 38.19 | 34.76 | 32.70 | 30.85 |
| | Stress Relaxation (%) | 0.00 | 55.89 | 61.81 | 65.24 | 67.30 | 69.15 |
| V7 | Stress Retention (%) | 100.00 | 45.59 | 39.05 | 35.31 | 33.11 | 31.58 |
| | Stress Relaxation (%) | 0.00 | 54.41 | 60.95 | 64.69 | 66.89 | 68.42 |
| V8 | Stress Retention (%) | 100.00 | 45.89 | 39.89 | 36.73 | 34.57 | 33.08 |
| | Stress Relaxation (%) | 0.00 | 54.11 | 60.11 | 63.27 | 65.43 | 66.92 |
| V9 | Stress Retention (%) | 100.00 | 47.64 | 42.08 | 39.15 | 36.98 | 35.55 |
| | Stress Relaxation (%) | 0.00 | 52.36 | 57.92 | 60.85 | 63.82 | 64.45 |

The term "stress retention" refers to the stress applied to the gloves from 0-5 minutes after the gloves has been stretched 100% of its original length, while the term "stress relaxation" is associated with the decrease in tensile stress after a duration of time under constant strain. A higher stress relaxation value is ideal as it indicates a more elastic and flexible glove.

The results in Table 6 show that all gloves V2 to V9 have a higher stress relaxation percentage from 0-5 minutes against the control. This is in line with the findings shown in Table 1, where the gloves had a lower modulus of elasticity and elongation at break % compared to glove V1. It is therefore emphasized again that the control glove pales in comparison when it comes to elasticity and flexibility compared to gloves V2-V9.

TABLE 7

Tear resistance of aged and unaged gloves at a thickness of 0.1 mm

| | Unaged | | Aged | |
|---|---|---|---|---|
| | Thickness (mm) | Load (N) | Thickness (mm) | Load (N) |
| V1 | 0.1 | 0.81 | 0.1 | 0.84 |
| V2 | 0.1 | 0.82 | 0.1 | 0.9 |
| V3 | 0.1 | 0.71 | 0.1 | 0.75 |
| V4 | 0.1 | 1.46 | 0.1 | 1.35 |
| V5 | 0.1 | 1.03 | 0.1 | 1.16 |
| V6 | 0.1 | 0.96 | 0.1 | 1.13 |
| V7 | 0.1 | 0.59 | 0.1 | 0.75 |
| V8 | 0.1 | 1.68 | 0.1 | 1.4 |
| V9 | 0.1 | 1.09 | 0.1 | 1.22 |

Overall, apart from V3 and V7, all the unaged and aged gloves with additives were able to withstand a heavier load before tearing when compared against the control. The gloves are therefore able to provide users with increased protection compared to the control.

TABLE 8

Durability of the gloves at 0.08 mm

| | Thickness | Results |
|---|---|---|
| V1 | 0.08 mm | Break after 4 hours |
| V2 | 0.08 mm | The sample did not break after 72 hours |
| V3 | 0.08 mm | The sample did not break after 72 hours |
| V4 | 0.08 mm | Break after 4 hours |
| V5 | 0.08 mm | Break after 4 hours |
| V6 | 0.08 mm | The sample did not break after 120 hours |
| V7 | 0.08 mm | The sample did not break after 120 hours |
| V8 | 0.08 mm | Break after 16.5 hours |
| V9 | 0.08 mm | Break after 16.5 hours |

The durability of the gloves was tested at 0.08 mm using an inhouse testing machine. An upper part of the glove was pulled up and down with an upper clamp, while a lower clamp secured the lower part of the glove in position. A cycle counter was present to record the cycle count of the upper clamp.

The time taken before the glove broke was calculated below:

$$\text{Time(min)} = \frac{\text{Cycle Number} \times 13}{60}$$

where 13 is the time taken per cycle in second, and 60 is conversion factor from second to minutes.

A testing medium, artificial sweat, was also included during the testing to stimulate real glove application.

The majority of gloves with an additive showed an improvement over the control glove. Gloves V2, V3, and V6 to V9 indicate that the gloves were more durable than the control, which broke after 4 hours. Again, this indicates the gloves offered users better protection compared to the control.

TABLE 9

Friction of the outer side of the gloves

| Formulation | Area | Static $\mu_s$ (Static coefficient of friction) | Kinetic $\mu_k$ (Kinetic coefficient of friction) |
|---|---|---|---|
| V1 | Outer Side | 1.163 | 1.103 |
| V2 | Outer Side | 1.358 | 1.329 |
| V3 | Outer Side | 1.312 | 1.241 |
| V4 | Outer Side | 1.324 | 1.232 |
| V5 | Outer Side | 1.333 | 1.321 |
| V6 | Outer Side | 1.385 | 1.327 |
| V7 | Outer Side | 1.398 | 1.32 |
| V8 | Outer Side | 1.319 | 1.233 |
| V9 | Outer Side | 1.365 | 1.345 |

\* static coefficient of friction is the maximum force required to move an object
\* kinetic coefficient of friction is the force produced during the movement of an object The friction on the outer surface of the glove was tested by determining the amount of force required for a puller to pull a glove sample with a standard weight block on it.

As seen above, the control glove recorded the lowest static coefficient of friction value, indicating that there is less friction on the surface of the glove. The control glove is thus more likely to have less control and grip when in contact with water or liquids as compared to gloves V2-V9.

TABLE 10

Puncture resistance of the gloves at 0.10 mm

| | Thickness (mm) | Max Load (N) |
|---|---|---|
| V1 | 0.10 | 4.13 |
| V2 | 0.10 | 6.04 |
| V3 | 0.10 | 5.09 |
| V4 | 0.10 | 5.52 |
| V5 | 0.10 | 5.15 |
| V6 | 0.10 | 5.12 |
| V7 | 0.10 | 4.92 |
| V8 | 0.10 | 5.29 |
| V9 | 0.10 | 4.93 |

Finally, Table 10 above indicates the puncture resistance of the gloves at 0.10 mm. A puncture needle with a load is pushed against a glove, until a puncture is recorded and observed on the glove.

It is easily observable from Table 10 that there in an improvement in the puncture resistance of all gloves V2-V9 when compared against the control glove.

Based on the results above, at least half or more of gloves were found to have similar, if not improved, properties when compared against the control glove. Again, this is significant as the composition as disclosed, when manufactured into a glove, is able to overcome, or at least reduce the current limitations of NBR gloves, particularly in terms of the flexibility and softness of the glove.

Even more beneficially is that the gloves with additives were able to provide adequate protection to its users despite being as thin as 0.08 mm. The thinness of the glove, coupled with the improvement in flexibility and softness of the gloves, is especially beneficial for surgeons and medical practitioners, as it does not limit the movement or dexterity of their fingers.

Importantly, it should be highlighted that all the gloves with additives were found to have a higher friction on the surface of the glove when compared to the control glove. The increase in friction on the surface of the gloves will allow for more control and grip when the gloves are donned, especially under wet or slippery conditions.

Other benefits of the embodiments further include a decrease of cleaning time and effort. The silane compound, i.e. the mixture of silicon dioxide and 2-amino-2 methylpropanol, and the liquid fluorocarbon added to the composition function as an anti-tack and mould releasing agents. The ability of the composition to function as its own anti-tack agent and mould releasing agent decreases the need for the addition of anti-tack agents such as carbonate and metal stearate in the coagulant formulation, as carbonate and metal stearate can be potential contaminants if the mould is not cleaned properly.

As the article is able to be removed easily from the mould, and without the addition of carbonate or metal stearates, the cleaning time is thus reduced, resulting in a decrease in the use of chemicals and water, and subsequently resulting in less harm to the environment.

Even more advantageously, the addition of liquid fluorocarbon also increases the durability, tear resistance, and elasticity of an elastomeric article produced from the current disclosure of the embodiments.

No part of any of the embodiments above comprise sulphur or accelerators, which are known to be potential contaminants and capable of inducing an allergic reaction in users.

In addition, the composition also describes embodiments where zinc oxide is not added, thus enabling the production of a soft and stretchable or flexible elastomeric article. Subsequently, these embodiments are less harmful to the environment, as less effort is used in the water treatment process without the presence of zinc oxide.

The embodiments as disclosed are therefore able to overcome, or at least reduce, the limitations and disadvantages of conventional gloves.

The present invention has thus been described in specific embodiments. It should not, however, be limited to the invention as disclosed, and it will be apparent to those skilled in the art that various changes and modifications may be made to the invention without departing from the scope of the invention.

The invention claimed is:

1. A composition comprising:
    an elastomer in an amount of from 51 to 98% weight of the composition;
    tetrafluoroethylene in an amount from 0.5 to 15% weight of the composition;
    a mixture in an amount from 1 to 5% weight of the composition, the mixture comprising silicon dioxide in an amount of from 10 to 30% weight of the mixture, 2-amino-2 methylpropanol in an amount from 1 to 3% weight of the mixture, surfactant in an amount from 2 to 5% weight of the mixture, dispersant, and water in an amount from 62 to 87% weight of the mixture; and
    a crosslinker in an amount from 0.5 to 10% weight of the composition, the crosslinker having a formula of

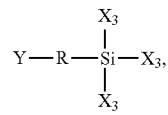

wherein Y is an epoxy group;
R is a linking group between the functional group Y and a silicon atom, wherein R is propylene or ethylene;
Si is silicon atom; and
$X_3$ are hydrolysable groups selected from methoxy, ethoxy, or isopropoxy.

2. The composition according to claim 1, wherein the elastomer comprises any one of polyurethane rubber, synthetic polyisoprene rubber, natural rubber, acrylonitrile butadiene rubber, styrene butadiene rubber, butadiene rubber, or polychloroprene.

3. The composition according to claim 2, wherein the elastomer selected from acrylonitrile butadiene rubber, polychloroprene rubber, styrene butadiene rubber, or butadiene rubber, is carboxylated.

4. The composition according to claim 2, wherein the elastomer selected from polychloroprene comprises an activator.

5. The composition according to claim 4, comprising 0.1 to 3% weight of the activator.

6. The composition according to claim 1, comprising 0.1 to 5% weight of antioxidant.

7. The composition according to claim 1, comprising 2 to 3% weight of liquid surfactant.

8. The composition according to claim 1 for the production of an elastomeric article manufactured through a dipping process.

9. The composition according to claim 1 for the production of a glove.

* * * * *